United States Patent [19]

Hughes

[11] Patent Number: 4,906,276

[45] Date of Patent: * Mar. 6, 1990

[54] PLANT TRANSPLANT AND PLANT PRESERVATION MEDIUM

[75] Inventor: John Hughes, Arlington Heights, Ill.

[73] Assignee: American Colloid Company, Arlington Heights, Ill.

[*] Notice: The portion of the term of this patent subsequent to Jun. 30, 2004 has been disclaimed.

[21] Appl. No.: 926,210

[22] Filed: Nov. 3, 1986

[51] Int. Cl.$^4$ .............................................. A01N 33/00
[52] U.S. Cl. ........................................... 71/77; 71/79; 71/68; 71/106; 71/118
[58] Field of Search ............................... 71/77; 47/56.7

[56] References Cited

U.S. PATENT DOCUMENTS

| | | | |
|---|---|---|---|
| 4,241,537 | 12/1980 | Wood | 47/57.6 |
| 4,525,527 | 6/1985 | Takeda et al. | 524/831 |
| 4,552,938 | 11/1985 | Mikita et al. | 526/240 |
| 4,677,174 | 6/1987 | Alexander et al. | 526/240 |

*Primary Examiner*—Glennon H. Hollrah
*Assistant Examiner*—Amelia A. Owens
*Attorney, Agent, or Firm*—Mason, Kolehmainen, Rathburn & Wyss

[57] ABSTRACT

A method of improving the crop yield of transplanted crops and of extending the useful life of freshly cut plants utilizing an aqueous gel including a highly absorbent, crosslinked, mixed salt of homopolymerized or copolymerized acrylic acid. The aqueous gels utilized in the present invention not only show improved crop yield and extended plant life in the absence of plant nutrients, but also exhibit sufficient gel strength and rigidity to support the plants in the absence of inert solid aggregates.

12 Claims, No Drawings

4,906,276

PLANT TRANSPLANT AND PLANT PRESERVATION MEDIUM

FIELD OF THE INVENTION

The present invention relates to a method of improving the crop yield of plants transplanted from a germination site, such as a greenhouse, to the field, and to a method of preserving and extending the useful life of freshly cut plants. More particularly, the present invention relates to a method of improving the crop yield of transplanted plants and of preserving the life of freshly cut plants by utilizing an aqueous gel including a highly absorbent, crosslinked, mixed salt of homopolymerized or copolymerized acrylic acid. The mixed salt of the polymerized acrylic acid forms an aqueous gel strong enough to support the stem of a plant in the absence of inert solid aggregates, and, surprisingly, both extends the plant life of freshly cut plants and the crop yield of transplanted plants in the absence of plant nutrients, growth promoters or other similar agricultural and/or horticultural adjuvants.

BACKGROUND OF THE INVENTION

Highly absorbent, crosslinked polymers have found wide use in a variety of applications, including sanitary goods, hygienic goods, water retaining agents, dehydrating agents, sludge coagulants, condensation preventing agents and release control agents for various chemicals. Water-absorbent polymers are available in a variety of chemical forms including substituted and unsubstituted natural and synthetic polymers such as hydrolysis products of starch-acrylonitrile graft polymers, carboxymethylcellulose, crosslinked polyacrylates, polyvinyl alcohols, polyacrylonitrile, polyvinylpyrrolidones, sulfonated polystyrenes, hydrolized polyacrylamides and polyethylene oxide.

In addition, aqueous gels, formed from the highly-absorbent crosslinked polymers of the present invention, have shown unexpected utility both in increasing the crop yield of transplanted plants and in preserving freshly cut plants. These results are more surprising considering that it is not necessary to incorporate primary plant nutrients, micronutrients, growth promoters or other agricultural and/or horticultural adjuvants into the gel to either extend the life of freshly cut plants or to increase the crop yields of transplanted plants. Unexpectedly, it has also been found that aqueous gels including a mixed salt of homopolymerized or copolymerized acrylic acid generate higher crop yields when fertilizers are excluded from the aqueous gels.

It has also been found that it is unnecessary to admix inert solid aggregates, such as sand, rock, woodflour or vermiculite, with the mixed salt of the polymerized acrylic acid in order to help support freshly cut plants. The aqueous gels formed from the mixed salt polyacrylates of the present invention are of sufficient strength and rigidity to hold the plants upright, and also allow the plant to withdraw the necessary water from the gel to preserve plant life.

Water-absorbent polymers have been used both to preserve freshly cut ornamental plants and as a growth medium for seeds, seedlings and transplants. U.S. Pat. No. 2,971,292 discloses a number of gel-forming colloidal materials, including polyacrylic polymers, that preserve the life of freshly cut plants. However, this patent stresses the use of plant nutrients and the use of an inert solid aggregate filler to free water from the gel and thus make the water available for plant uptake. As will be seen in the detailed description of the invention, the inclusion of plant nutrients and inert solid aggregates into gels made from the polymers of the present invention is unnecessary, and is possibly detrimental.

Other patents disclosing the use of water absorbent polymers for use in plant preservation or as a plant growth medium include: U.S. Pat. No. 4,124,748, wherein a crosslinked copolymer of a vinyl ester and an unsaturated carboxylic acid ester, neutralized with a potassium or ammonium alkali, is suggested as a seed culturing media for plants; U.S. Pat. No. 4,241,537, wherein a nonionic, monolithic, crosslinked polyurethane is used as a soil plug for growing plants; U.S. Pat. No. 4,559,074, wherein a substantially nonionic crosslinked polyacrylamide is used as an additive for a plant growth medium; U.S. Pat. No. 4,238,374, wherein a water-insoluble crosslinked polymer and inert aggregate particles are utilized to preserve floral arrangements; U.S. Pat. No. 4,320,040, wherein a polyvinyl alcohol and polymerized acrylic acid composition is used as a water-retaining agent for plants or soils; and U.S. Pat. No. 3,336,129, wherein an absorbent crosslinked polymer and sand or soil are admixed to form plant growth modifiers.

Several other U.S. Patents disclose polymers used in plant growth media, including U.S. Pat. Nos. 3,373,009; 3,900,378; 3,973,355; 4,034,508; 3,831,317; 4,495,310; 4,439,552; and 4,329,436.

The methods and compositions disclosed in the prior art require or recommend the inclusion of fertilizers and/or solid aggregates into the gels formed from the water-absorbent polymer. In addition, several of the prior art methods are difficult or impractical to use since: the compositions are not readily dispersed in water; the polymer, such as a starch-acrylonitrile graft polymer, is expensive and difficult to make; the polymer is subject to hydrolysis or bacterial degradation unless parameters, such as pH, are carefully controlled; the physical parameters, such as pH, necessary to protect the integrity of the polymer may adversely affect certain plants; and the polymers produce a gel that does not readily surrender water to the plants.

Therefore, it would be extremely advantageous to provide a method of extending the life of freshly cut plants and of increasing the crop yield of transplanted plants by utilizing an aqueous gel including an economical, easy to synthesize and disperse, non-degrading, water-absorbent polymer. It would also be advantageous if the polymer would generate gels of sufficient gel strengths to support the stems of the plant without the need of inert solid aggregates, yet be able to release the necessary water to the plant on demand. Finally, it would be most advantageous if aqueous gels formed from the polymer could be used without the addition of fertilizers and the like while providing nutrients to the plant, both with respect to economy and ease of gel formation.

Any method utilizing a polymer having the above-described qualities to extend plant life or increase crop yield would enhance and broaden the use of water-absorbent polymers in the agricultural and horticultural areas. Preferably, any such method should utilize an economical, easy-to-manufacture polymer that possesses qualities necessary to support plant life and that can be used at low percentages.

SUMMARY OF THE INVENTION

In brief, the present invention is directed to a method of improving the crop yield of transplanted plants and of preserving fresh cut plants by utilizing an aqueous gel including a highly-absorbent, crosslinked salt of a polyacrylate polymer. It has been found that the crop yields and the length of useful plant life are increased by utilizing an aqueous gel of the polyacrylate salt in the absence of primary or secondary plant nutrients and/or in the absence of inert solid aggregates.

In accordance with the present invention, an aqueous gel, formed from a mixed salt of a highly-absorbent, crosslinked homopolymer or copolymer of acrylic acid, can improve the crop yield of plants transplanted from a germination site, such as a greenhouse, to the field and can extend the useful life of freshly cut plants. The method of the present invention has been found especially effective when an aqueous gel formed from the mixed salt of a crosslinked homopolymerized or copolymerized acrylic acid is used in the absence of an inert solid aggregate or a fertilizer or other plant nutrient.

Therefore, the present invention is directed to a method of improving the crop yields of transplanted plants and of preserving freshly cut plants with an aqueous gel including a mixed salt of a water-absorbent, crosslinked homopolymer or copolymer of acrylic acid. The mixed salt of the polymers utilized in the present invention has unexpectedly and surprisingly shown increased crop yield for transplanted plants when compared to similar non-mixed salts of polyacrylic acid.

More particularly, the present invention is directed to a method of improving the crop yields of transplanted plants and of extending the life of freshly cut flowers by utilizing an aqueous gel including a homopolymer or copolymer of acrylic acid that is neutralized with both potassium and ammonium alkalis. Compared to polymers of similar structure, the polymers used in the method of the present invention have shown a superior ability to increase crop yield and extend plant life. Without being limited to any particular mechanism, it is theorized that such improvements in crop yield and length of plant life are due to the method of manufacture of the polymer wherein a heated aqueous solution comprising (A) acrylic acid neutralized 70 to 100 mole percent with ammonium and potassium alkalis; and (B) a water-miscible to water-soluble polyvinyl monomer, and water and having a combined monomer concentration of (A) plus (B) of 30 to 80 wt. % is subjected to polymerization in the presence of a polymerization initiator without external heating while allowing water to evaporate off. Takeda et al U.S. Pat. No. 4,525,527 and Mikita et al. U.S. Pat. No. 4,552,938 disclose methods for making similar polymers without the step of external heating.

Similarly, copolymers that are useful in the method of the present invention are synthesized by an aqueous polymerization of (A) acrylic acid neutralized 70 to 100 mole percent with ammonium, and potassium alkalis; with (B) styrene an amount of 1% to 25% based on the weight of acrylic acid or acrylate, computed as based on acrylic acid; and (C) a water-miscible or a water-soluble polyvinyl monomer in an amount of 0.001 to 0.3 weight percent based on the total weight of (A), (B) and (C).

Therefore, it is an object of the present invention to provide a method of increasing the crop yield of transplanted plants and of preserving freshly cut plants. It is also an object of the present invention to provide a method of increasing the crop yield of transplanted plants and of preserving freshly cut plants by utilizing an aqueous gel including a highly absorbent, crosslinked polymer.

Another object of the present invention is to provide a method of increasing the crop yield of transplanted plants and of preserving freshly cut plants by utilizing an aqueous gel including a mixed salt of a crosslinked, homopolymerized or copolymerized acrylic acid.

Another object of the present invention is to provide a method of increasing the crop yield of transplanted plants and of preserving freshly cut plants by utilizing a homopolymerized or copolymerized acrylic acid neutralized with both potassium and ammonium alkalis.

Another object of the present invention is to provide a method of increasing the yield of transplanted plants and of preserving freshly cut plants by synthesizing potassium and ammonium-neutralized, homopolymers and copolymers of acrylic acid that are suitable for supplying the crops and plants with the required water and nutrients for their continued growth and life.

Still another object of the present invention is to provide a method of increasing the crop yield of transplanted plants and of preserving freshly cut plants by utilizing an aqueous gel including the mixed potassium and ammonium salt of a homopolymer or copolymer of acrylic acid, in the absence of plant nutrients and agricultural and/or horticultural adjuvants or inert solid aggregates.

These and other objects and advantages of the present invention will become apparent from the following detailed description of the invention.

DETAILED DESCRIPTION OF THE INVENTION

In accordance with the present invention, an aqueous gel, formed from a highly absorbent, crosslinked polymer, unexpectedly and surprisingly improves the crop yield of transplanted plants and extends the life of freshly cut flowers. As will be discussed more fully hereinafter, the polymers used in the method of the present invention are mixed potassium and ammonium salts of a homopolymer or copolymer of acrylic acid. These polymers form aqueous gels that exhibit substantial increases in crop yields of transplanted plants in comparison to aqueous gels obtained from chemically similar polymers, and, quite surprisingly, exhibit a greater improvement in crop yields when fertilizers and other agricultural and/or horticultural adjuvants are absent from the gel.

Also, in the preservation of freshly cut plants, aqueous gels formed from the mixed salt polymers of acrylic acid are of sufficient strength to support the stem of the plant even in the absence of inert solid aggregates. In addition, the polymers used in the method of the present invention possess sufficient water-absorbing and swelling ability such that suitable gels are formed using very low percentages of polymers, therefore allowing a sufficient amount of free, unbound water available for plant uptake upon demand.

In addition to clays and natural gums, several types of water-absorbing crosslinked polymers have been used to form aqueous gels that are useful as a plant growth medium or plant preservation medium. However, the previous methods and compositions all possess disadvantages that severely limit their practical utility. For instance, gels made from clays are often difficult and messy to prepare; polymers based on natural gums or natural polymers, such as starch, are subject to chemical and bacterial degradation; some polymers must be used in a high percentage and may bind the water to such a degree that sufficient water is not available for use by the plant; polymers incapable of surrendering the water from the gel to the plant must be combined with inert solid aggregates in order to free some water for use by the plant; and some of the polymers utilized to make the gels are expensive and difficult to prepare.

As will become apparent from the following detailed description of the invention, the method of the present invention utilizes polymers that are easy and economical to synthesize, resist degradation and possess the requisite physical characteristics, such as gel strength, fast water-absorption and dispersibility, that makes them ideal for use in plant growth media and as a preservative for freshly cut plants. The method of the present invention utilizes polymers that are non-toxic to plants; are sufficiently crosslinked to be water-insoluble, yet are able to absorb water and swell and disperse in water; are effective at low percentages; form transparent gels; easily release absorbed-water from the gel to materials having a lower concentration of water than the gel; and are sufficiently inert such that the composition of the gel may include other common additives without adversely affecting the basic utility of the polymer.

The polymers that have found particular utility in the method of the present invention include the mixed salts of homopolymerized or copolymerized acrylic acid. More particularly, the potassium and ammonium mixed salts of polyacrylic acid, or the potassium and ammonium mixed salts of copolymers of acrylic acid and styrene may be used to form aqueous gels that increase the crop yield of transplanted plants and preserve freshly cut plants. However, to achieve the full advantage of the present invention, a polyacrylic acid, neutralized both with a potassium alkali and an ammonium alkali, is used to form an aqueous gel for improving crop yields and preserving freshly cut plants.

As will be more fully discussed hereinafter, according to the method of the present invention, an aqueous gel formed from the potassium and ammonium mixed salt of polyacrylic acid, or from the potassium and ammonium mixed salt of acrylic acid copolymerized with styrene surprisingly and unexpectedly increases the crop yields of transplanted plants in comparison to gels formed from chemically similar polymers. The polymers used in the method of the present invention are synthesized from a monomer mix including ammonium acrylate and potassium acrylate, theoretically accounting for the improved results over acrylic acid polymers that are neutralized after polymerization. Preneutralization of the monomer mix assures not only a more complete neutralization, but also a more random and even distribution of the ammonium and potassium ions along the polymer chain.

More particularly, polymers that can be used in the method of the present invention are synthesized by first preparing a hot aqueous solution comprised of acrylic acid neutralized 70 to 100 mole percent, a water-miscible or water-soluble polyvinyl monomer, water and, when desired, an organic solvent having a boiling point of 40° to 150° C., wherein the acrylate monomer and the polyvinyl monomer are present in a combined concentration of 30 to 80 wt. %. To achieve the full advantage of the present invention, the acrylate and polyvinyl monomers are present in a combined concentration of less than 70 weight percent of the monomer solution.

In accordance with another important embodiment of the present invention, the combined concentration of the acrylate and polyvinyl monomers is less than 55 weight percent of the monomer solution. The concentration of the monomers is deliberately determined considering the state of the solution (i.e., as to whether or not the monomers can be completely dissolved in water), ease of the reaction of the monomers, escape of the monomers due to the scattering during the reaction, and the like. The aqueous solution can be prepared easily by placing the acrylic acid, the strong potassium and ammonium alkalis, e.g. potassium hydroxide and ammonium hydroxide, for neutralizing the acid and the polyvinyl monomer into water in such amounts that the resulting solution has the above-mentioned monomer concentration. In accordance with one important embodiment of the present invention, the ratio of potassium ions to ammonium ions should range from approximately 70:30 to 30:70. To achieve the full advantage of the present invention the ratio of potassium ion to ammonium ions should range from approximately 55:45 to 45:55. To dissolve the monomer thoroughly, the mixture can be heated to an elevated temperature.

Although it is desirable to use the neutralizing agent usually in an amount sufficient to neutralize acrylic acid 100 mole %, there is no particular need to neutralize the acid 100% insofar as the neutralizing agents are used in such an amount as to achieve not less than about 70% neutralization. However, too large a quantity of free acrylic acid, if present in the aqueous solution, is likely to partly splash out of the reaction vessel, resulting in a loss during the reaction, leading to a reduced degree of polymerization. In some respects a definite amount of neutralized acrylic acid is desirable in that most freshly cut flowers and plants stay alive longer in water solutions that are slightly acid to neutral. The lower pH of gels formed from polymers having a definite amount of unneutralized acid also prevents mold formation and reduces the possibility of vascular blockage by bacteria that thrive at pH values of 7 or above. Except for the possibility of mold or bacteria growth, use of an excessive amount of the neutralizing agent will not raise any particular problem, but the excess does not participate in the polymerization reaction and is therefore useless and wasted.

In accordance with another important embodiment of the present invention, acrylic acid neutralized 70-100 mole percent is mixed with 1% to 25%, based on the weight of acrylic acid, styrene and a water-miscible or water-soluble polyvinyl monomer in an aqueous solution at a temperature of about 20° to 100° C. The solution is subjected to a polymerization reaction and a cross-linking reaction by the addition of a polymerization initiator. The polymerization reaction proceeds sufficiently within a very short period of time and if the monomer concentration is at least 30 percent by weight of the aqueous monomer mixture, the heat of the copolymerization and cross-linking reactions will evaporate water rapidly from the reaction system to form a dry solid (less than 15 percent by weight water) water absorbing resin without the need for any subsequent drying step. The solid can be easily pulverized into a powder suitable for the desired use.

The polyvinyl monomer used to crosslink the polymers of the present invention should be miscible with or soluble in water so that the monomers will be uniformly dissolved or dispersed in the aqueous solution of the monomer mixture. Examples of such polyvinyl monomers include bisacrylamides such as N,N'-methylenebisacrylamide and N,N'-methylenebismethacrylamide; polyacrylic (or polymethacrylic) acid esters represented by the following formula (I); and diacrylamides represented by the following formula (II). Among these, especially preferably are N,N'-methylenebisacrylamide, N,N'-methylenebismethacrylamide and like bisacrylamides.

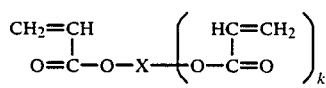

Formula (I)

wherein X is ethylene, propylene, trimethylene, hexamethylene, 2-hydroxypropylene, $(CH_2CH_2O)_nCH_2CH_2—$ or

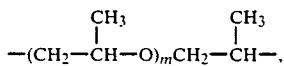

n and m are each an integer of from 5 to 40, and k is 1 or 2.

Formula (II):

wherein l is 2 or 3.

The polyvinyl monomer is used in an amount of about 0.001 to 0.3 wt. % of the combined amount of acrylic acid and styrene monomers in the aqueous monomer mixture. In accordance with another important embodiment of the present invention, the polyvinyl monomer cross-linking agent should be present in the aqueous solution in an amount of at least 0.2 wt. % based on the total weight of monomers to provide a resin sufficiently cross-linked to avoid water solubility. If the polyvinyl monomer is included in the aqueous solution in an amount of 0.2 to 0.6 weight percent based on the weight of neutralized acrylic acid and polyvinyl monomers, the resulting polymer will have a sufficient degree of crosslinking to avoid solubilization on absorption of water.

The aqueous mixed monomer solution is heated and thereafter subjected to polymerization or copolymerization and cross-linking reactions with the addition of a polymerization initiator. Although the temperature of the aqueous mixed monomer solution is not particularly limited since the mixed monomer solution is initiated into polymerization by the addition of the initiator, the temperature is usually about 50° to about 85° C., preferably about 60° to about 75° C.

Various polymerization initiators are usable that are known for use in preparing polyacrylates. Examples of useful initiators are redox initiators comprising a reducing agent, such as a sulfite or bisulfite of an alkali metal, ammonium sulfite or ammonium bisulfite, and an initiator, such as a persulfate of an alkali metal or ammonium persulfate, in combination with the reducing agent; azo initiators including azobisisobutyronitrile, 4-t-butylazo-4'-cyanovaleric acid, 4,4'-azobis(4-cyanovaleric acid) and 2,2'-azobis(2-amidinopropane) hydrochloride; trimethylolpropane triacrylate; and the like. These initiators can be used singly or in a suitable combination. Of these, especially preferable are a redox initiator composed of ammonium persulfate and sodium hydrogen sulfite, and azo initiators such as azobisisobutyronitrile and 2,2'-azobis(2-amidinopropane)hydrochloride. The initiators are advantageously used usually in the form of an aqueous solution but can be used as diluted with a suitable solvent. The initiator is used in a usual amount, i.e., in an amount, calculated as solids, of about 0.1 to about 10%, preferably about 0.5 to about 5%, of the combined weight of the monomers, namely acrylate (and free acrylic acid); styrene (if any); and polyvinyl monomer cross-linking agent. Depending on the amount and kind of the initiator, the initiator is usable together with isopropyl alcohol, alkylmercaptan or other chain transfer agents to control the molecular weight of the polyacrylate copolymer to be obtained.

The following Examples are illustrative of the polymers that may be utilized in the method of the present invention.

EXAMPLE 1

To deionized water in a storage vessel is added, wherein percents are weight percents based on the total weight of the monomer solution formed, 58.81% acrylic acid first, then 11.76% potassium hydroxide and 11.76% ammonium carbonate and 14.70% ammonium hydroxide serving as neutralizing agents. Thereafter 0.03% of N, N-methylenebisacrylamide as a polyvinyl monomer is added to prepare an aqueous solution of potassium acrylate and ammonium acrylate in 2.79% of water having a neutralization degree of about 90% and a combined monomer concentration of 58.84 wt. %. The monomer solution is held in a storage vessel until the polymer solution process begins by feeding polymerization initiator from a second storage vessel simultaneously with monomer solution from the first storage vessel into the reaction vessel.

The aqueous solution is maintained at 70° C., and with the solution in reaction vessel 30 are continuously admixed to maintain a concentration of 0.15% of 2,2-azobis(2-amidino-propane)hydrochloride. The final solution is as follows:

| CHEMICALS | PERCENT |
|---|---|
| ACRYLIC ACID | 58.81% |
| POTASSIUM HYDROXIDE | 11.76% |
| AMMONIUM CARBONATE | 11.76% |
| N,N—METHYLENEBISACRYLAMIDE | 0.03% |
| POLYMERIZATION INITIATORS | 0.15% |
| AMMONIUM HYDROXIDE | 14.70% |
| (30% aqueous ammonia) | |
| WATER | 2.79% |
| TOTAL | 100.00 |

The polymer is allowed to complete curing for about 30 minutes at ambient temperature to give a dry solid mass of cross-linked potassium and ammonium polyacrylate product having a water content of 11% and a residual monomer concentration of 1200 ppm. The resin is made into a powder by a pulverizer.

EXAMPLE 2

The following mixed monomer solution was reacted in the same manner as described in Example 1 to give a dry solid mass of crosslinked potassium/ammonium polyacrylate.

| CHEMICALS | PARTS BY WEIGHT | PERCENT |
|---|---|---|
| ACRYLIC ACID | 16.80 | 54.15% |
| AMMONIUM HYDROXIDE (30% aqueous ammonia) | 4.20 | 13.54% |
| POTASSIUM HYDROXIDE | 4.20 | 13.54% |
| AZO INITIATOR | 0.13 | 0.42% |
| GPTA (glycerol propoxy triacrylate molecular weight 428.5) | 0.002 | 0.01% |
| AMMONIUM CARBONATE | 3.31 | 10.67% |
| WATER | 2.30 | 7.67% |
| TOTAL | 30.94 | 100.00% |

EXAMPLE 3

| CHEMICAL | PARTS BY WEIGHT | PERCENT |
|---|---|---|
| ACRYLIC ACID | 16.80 | 53.57% |
| AMMONIUM HYDROXIDE (30% aqueous ammonia) | 4.20 | 13.39% |
| POTASSIUM HYDROXIDE | 4.20 | 13.39% |
| STYRENE | 0.81 | 1.08% |
| GPTA (glycerol propoxytriacrylate molecular weight 428.5) | 0.002 | 0.01% |
| AMMONIUM CARBONATE | 3.31 | 10.55% |
| WATER | 2.38 | 7.59% |
| TOTAL | 31.36 | 100.00% |

EXAMPLE 4

| CHEMICALS | PERCENT |
|---|---|
| ACRYLIC ACID | 58.23% |
| STYRENE | 1.58% |
| POTASSIUM HYDROXIDE | 11.76% |
| AMMONIUM CARBONATE | 11.76% |
| N,N—METHYLENEBISACRYLAMIDE | 0.03% |
| AZO POLYMERIZATION INITIATORS (5% wt. aqueous) | 0.15% |
| AMMONIUM HYDROXIDE (30% wt. aqueous ammonia) | 14.70% |
| WATER | 1.79% |
| TOTAL | 100.00% |

The mixture is poured onto a traveling endless belt and spread thereover in the form of a layer about 10 mm in thickness. About 30 seconds thereafter, the mixture starts to polymerize, and the reaction is completed in about 1 minute. The maximum temperature of the mixture during the reaction is about 120° C.

The copolymer is allowed to complete curing for about 30 minutes at ambient temperature to give a dry solid strip of potassium/ammonium polyacrylate and polyacrylic-polystyrene product having a water content of 11% and a residual monomer concentration of 1200 ppm. The strip is made into a powder by a pulverizer.

EXAMPLE 5

The following mixed monomer solution was reacted in the same manner as described in Example 4 to give a dry solid strip of potassium/ammonium polyacrylate and polyacrylic-polystyrene product of low water content and low residual monomer concentration.

| CHEMICALS | PERCENT |
|---|---|
| ACRYLIC ACID | 56.01% |
| STYRENE | 2.80% |
| POTASSIUM HYDROXIDE | 11.76% |
| AMMONIUM CARBONATE | 11.76% |
| N,N—METHYLENEBISACRYLAMIDE | 0.03% |
| AZO POLYMERIZATION INITIATOR (5% wt. aqueous) | 0.15% |
| AMMONIUM HYDROXIDE (30% wt. aqueous ammonia) | 14.70% |
| WATER | 2.79% |
| TOTAL | 100.00% |

A highly-absorbent, crosslinked polymer, synthesized according to the method of Example 1, was tested for its ability to prolong the life of freshly cut flowers. An aqueous gel, made by dispersing approximately 0.1% by weight of the crosslinked, insoluble mixed potassium/ammonium polyacrylate synthesized according to the method of Example 1 in tap water, was tested for its ability to extend the useful life of freshly cut roses. It was found that this low percentage of polymer generated gels of sufficient consistency and gel strength to support the flower stems in an upright position. In these tests, water is first added to the vase, then the mixed salt polyacrylate is added slowly to the water and dispersed. It is not necessary, or desirable, to use hot water to disperse to polymer. The dispersion is not a dissolving process, but a physical water-absorption and polymer-swelling process, wherein the polymer absorbs many times its weight in water and swells many times its volume. The use of hot water may adversely affect the plants inserted into the gel.

Within a few minutes of its addition to the water, the mixed salt polyacrylate has absorbed sufficient water to swell and form a gel of the desired gel strength. Freshly-cut roses were inserted into the gel and each day were visually compared to roses inserted into plain tap water for signs of wilting and death. The roses were considered to have expired when the petals wilted and fell. The roses inserted into the gel made from the mixed salt polyacrylate lived a total of fourteen days, compared to seven days for roses placed in plain tap water.

Prior art methods require a relatively large amount of gellant to generate a gel of sufficient consistency and strength to support freshly cut flowers and plants. The prior art also teaches that increasing the percentage of polymer in the gel reduces the preservation qualities of the gel. For instance, in U.S. Pat. No. 4,238,374, increasing the amount of a monovalent salt of polyacrylic acid to coat the inert solid aggregate of the mixture resulted in the flowers dying four days earlier than in gels utilizing a lower percentage of polymer. This result has been attributed to a gel thickness that is too great for water uptake by the plants. Therefore, an important factor in the usefulness of the present invention in preserving freshly cut plants is the low percentage of from about 0.02% to about 0.3%, and preferably from about 0.05% to about 0.2% of potassium/ammonium acrylate polymer that is necessary to obtain these unexpected results.

Another important feature of the method of the present invention is the ability of the potassium/ammonium polyacrylate polymer to easily give up its absorbed water to the plant upon demand. Several polymers generate gels of sufficient strength and consistency to support freshly cut plants, however, the absorbed water is bound so tightly that it is not available to the plant, and as a result, inert solid aggregates must be added to free some water for use by the plants. In addition, the polymers that are useful in the present invention are able to supply the freshly cut plants with the potassium and nitrogen the plants require for extended life. The prior art discloses that flowers are preserved better in a gel, particularly if the gel contains plant nutrients. The polymers used in the method of the present invention have plant nutrients incorporated in the polymeric structure that, surprisingly, are available to the plant should the plant require them.

In short, the materials and methods of the prior art have provided inferior and impractical supports for floral and plant arrangements in that either support is lacking and/or inadequate water is provided to cut flower arrangements. The method of the present invention avoids these problems by forming an aqueous gel from a low percentage of an ammonium/potassium mixed salt polyacrylate that supports any plant grown for ornamental purposes. The shape of the vase or container is immaterial, and the gel strength is sufficient to maintain the floral arrangement in place for days, whether the plants are inserted vertically or at an angle. The method of the present invention generates gels that can support freshly cut flowers, dried flowers, non-flowering cut ornamentals, ferns, artificial flowers, plastic ornamentals, candles, and other such plants and decorative articles. The arrangements can be easily rearranged by removing the plant stem or decorative article then reinserting it in the desired position. The gel will self-heal, whereby the hole obtained by removing the stem will automatically close. After plant death, or when otherwise desired, the arrangement may be dismantled and the gel easily rinsed from the container.

In addition to the above-described benefits, utilizing the gels of the method of the present invention affords the further benefits of reducing water spillage, acting as a synthetic soil to supply the plants with their water and nutrient needs, and ease, speed and economics of gel formation. Although the addition of fertilizers or other agricultural and/or horticultural adjuvants is not required to obtain the beneficial results of the present invention, these additives and other common additives may be incorporated into the gels of the present invention as long as the basic utility of the present invention is not affected. Such additives include colorants to give the gel an ornamental effect, such as a dye or a pigment, for example iron oxide, chromium oxide or copper oxide; buffering agents to help preserve pH sensitive plants; pH adjusters such as boric acid, acetic acid, or citric acid; chemical preservatives, such as sucrose; anti-bacterial agents, such as 8hydroxyquinoline citrate; respiration inhibitors; and inert solid aggregates, such as soil, sand, sawdust, woodflour, pumice, silica gel, ground corn cobs, rocks, vermiculite, attapulgite, flyash, perlite, and diatomaceous earth.

To demonstrate the new and unexpected results obtained by the method of the present invention, aqueous gels made from the mixed ammonium/potassium salts of the polyacrylates of the present invention were shown to increase the crop yield of transplanted plants and decrease losses in transplanted seedlings. For example, Tables I and II illustrate the effect of using an aqueous gel including a mixed potassium/ammonium salt of a polyacrylate of the present invention in the transplanting starter solution on the yield of Yolo Wonder L Peppers.

EXAMPLES 6-17

Ten week old pepper transplants were planted in a field, in rows 6.1 meters long with 0.9 meters between the rows. The plants were spaced 0.4 meters apart. Each plant received 200 ml. of starter solution and/or gel solution, applied to the roots in the planting hole. The hole was then covered with soil. Marketable yields were recorded after approximately 10 weeks, 13 weeks and 16 weeks after transplanting. The values in Table II for the pepper yields are the average of three replications. Table I lists the amount of polymer and/or starter fertilizer used in each example. Gels containing polymer and fertilizer (Ex. 13 through 17) required a higher percentage of polymer in order to maintain similar gel viscosities.

TABLE I

| EXAMPLES | TREATMENT | CONCENTRATION |
|---|---|---|
| 6 | Untreated | — |
| 7 | 12-48-8* (SOL-U-GRO) | 0.72% (wt/v) |
| 8 | TERRA-SORB GB | 0.60% (wt/v) |
| 9 | SUPRASORB-1000 | 0.60% (wt/v) |
| 10 | A.C. POLYMER | 0.60% (wt/v) |
| 11 | ABG-7005 | 0.41% (wt/v) |
| 12 | LIQUA-GEL | 0.60% (wt/v) |
| 13 | TERRA-SORB GB + 12-48-8* | 1.30% + 0.72% (wt/v) |
| 14 | SUPRASORB-1000 + 12-48-8* | 1.00% + 0.72% (wt/v) |
| 15 | A.C. POLYMER + 12-48-8* | 1.50% + 0.72% (wt/v) |
| 16 | ABG-7005 + 12-48-8* | 1.04% + 0.72% (wt/v) |
| 17 | LIQUA-GEL + 12-48-8* | 1.20% + 0.72% (wt/v) |

*Starter fertilizer solution containing 12% by weight nitrogen as N; 48% by weight phosphorus by weight as $P_2O_5$ and 8% potassium by weight as $K_2O$.

As set forth in the following in Table II, Examples 7 through 17 are compared to the untreated control Example 6. Example 7 contains only a fertilizer solution, whereas Examples 8, 9, 11 and 12 are aqueous gels containing only competitive crosslinked polyacrylate polymers. These competitive polymers are potassium polyacrylates, synthesized via inverse polymerization in a water-hydrocarbon solution. By this competitive polymerization process, the water-hydrocarbon solution is evaporated after polymerization, the polymer is dried, and the polymer is then ground to an appropriate size before use. The process of manufacture of these polymers is appreciably different from the method of manufacture of the polymers used in the present invention, theoretically accounting for the inferior results of these chemically-similar polymers when compared to the polymers utilized in the present invention.

The aqueous gel of Example 10 is formed from the mixed potassium/ammonium polyacrylates synthesized according to the method outlined in Example 1, and the aqueous gel of Example 15 is formed from the same potassium/ammonium polyacrylate in conjunction with the fertilizer solution of Example 7. The aqueous gels of Examples 13, 14, 16 and 17 are formed from competitive crosslinked polymers in conjunction with the starter fertilizer of Example 7. Table II illustrates the effect of the solutions and gels of Examples 6 through 17 on the yield of Yolo Wonder L Peppers.

TABLE II

Effect of Gels on the Yield of Yolo Wonder L Peppers

| EXAMPLE NUMBER | TOTAL NUMBER OF FRUIT | TOTAL WT. FRUIT (Kg) | WT. FRUIT PER PLANT (Kg) |
|---|---|---|---|
| 6 | 90.33 | 13.30 | 1.00 |
| 7 | 97.67 | 13.97 | 1.03 |
| 8 | 100.67 | 13.46 | 1.01 |
| 9 | 68.00 | 8.41 | 0.59 |
| 10 | 132.00 | 18.24 | 1.27 |
| 11 | 104.67 | 13.76 | 0.92 |
| 12 | 113.67 | 16.80 | 1.12 |
| 13 | 106.00 | 14.73 | 1.00 |
| 14 | 62.00 | 8.07 | 0.69 |
| 15 | 111.00 | 15.39 | 1.13 |
| 16 | 112.00 | 15.37 | 1.06 |
| 17 | 117.67 | 16.32 | 1.19 |

It is most surprising and unexpected that aqueous gels made from the mixed potassium/ammonium salt of crosslinked polyacrylic acid (Example 10) not only demonstrate improved yields in total number of fruit, total weight of fruit, and the weight of fruit per plant compared to the untreated control (Example 6), but all three yield measurements also are improved when compared to using starter fertilizer alone (Example 7), and when compared to an aqueous gel including starter fertilizer and the mixed potassium/ammonium salt of crosslinked polyacrylic acid (Example 15). The aqueous gel containing the mixed potassium/ammonium salt of crosslinked polyacrylic acid (Example 10) of the present invention also shows improved yields over each of the competitive polymers, both when the competitive product is used alone and unless the competitive product is used in conjunction with the starter fertilizer.

To illustrate, Example 10, utilizing an aqueous gel containing only the potassium/ammonium polyacrylate synthesized according to the method of Example 1, shows a 46% increase in the total number of fruit, a 37% increase in the total weight of fruit, and a 27% increase in the weight of fruit per plant over the untreated control of Example 6. Likewise, Example 10 shows respective yield increases of 35%, 30% and 23% over Example 7, that utilizes a transplanting fertilizer solution. It is completely unexpected for the mixed ammonium/potassium polyacrylate salts used in accordance with the present invention to outperform transplant fertilizer solutions. Surprisingly, the assumed and expected further yield improvements from adding a fertilizer to an aqueous gel formed from the mixed ammonium/potassium polyacrylate salt is not observed. As seen in Example 15, this combination exhibits yields that are improved over the use of fertilizers alone (Example 7), but gives yields that are well below those obtained using an aqueous gel including the mixed ammonium/potassium polyacrylate salt but absent fertilizer (Example 10).

In every case, the mixed ammonium/potassium polyacrylate salt (Example 10) used in the method of the present invention gave improved yields over the competitive gel-forming polymers of Examples 8, 9, 11 and 12. Yield results from tests using competitive polymers to form the aqueous gel ranged from 20% to 70% lower in total number of fruit, 11% to 73% lower in total weight of fruit, and 15% to 96% lower in weight of fruit per plant compared to the yield results of Example 10. In tests combining aqueous gels formed from competitive polymers with fertilizers, some examples exhibited improved yields over the aqueous gels using the competitive polymer alone, and examples exhibited decreased yields from aqueous gels using the competitive polymer alone, however, in none of the tests were the yields improved to a greater degree than the increases observed in using the mixed ammonium/potassium polyacrylate salts (Example 10).

As previously stated, the mixed polyacrylate salt of the present invention has nitrogen and potassium available for use by the transplanted plant or the seedling. In addition, these mixed salt polyacrylates have the ability to release water to the plant upon demand, since the polymer does not bind the water to the extent that the water is unavailable to plant. Such a result is surprising and unexpected for polymers that have such high water-retention capacities. It is a particular and distinct advantage of these mixed ammonium/potassium polyacrylate salts that they have the ability to retain large amounts of water and that they also have the ability to surrender that water to the plant on demand. These unique capabilities thereby reduce moisture stress on the plants during dry or drought periods. The polymers useful in the method of the present invention are capable of preferentially absorbing the water in relation to soil, and will hold the moisture for release upon demand to the roots contacting the polymer. By reducing the stress effects from the lack of moisture, the loss of transplanted seedlings is reduced and crop yields are directly increased.

The method of the present invention also can be used to improve the crop yields of any other cash crops such as sweet corn, brussels sprouts, beans, tomatoes and strawberries, or to reduce the number of lost transplants in plants such as tobacco, annuals and perennials, woody plants and ornamentals.

It should be understood that the present disclosure has been made only by way of preferred embodiment and that numerous changes in details of construction, combination and arrangement of parts may be resorted to without departing from the spirit and scope of the invention as hereunder claims.

What is claimed and sought to be secured by Letters Patent of the United States is:

1. A method of increasing the yield of a transplanted crop comprising insertion of a stem or root of the crop into a gel including water and a crosslinked, water-absorbent, mixed salt polyacrylate, wherein the crosslinked, water-absorbent, mixed salt polyacrylate is prepared by mixing a monomer solution of (A) acrylate acid neutralized 70-100 mole percent with a potassium alkali and an ammonium alkali; (B) styrene in an amount of 0% to 25% based on the weight of acrylic acid and (C) a water-miscible to water-soluble polyvinyl monomer in a combined concentration of (A), (B) and (C) of at least 30 wt. %; with water to form a mixed monomer solution wherein the monomers of the mixed monomer solution consist essentially of (A) and (B) and (C) and initiating polymerization of monomers (A), (B) and (C) such that during polymerization, the exothermic heat of reaction is substantially the only heat energy used to accomplish polymerization, cross-linking and to drive off sufficient water to obtain a solid cross-linked resin having a water content of 15 percent by weight or less.

2. The method of claim 1 wherein the combined concentration of the monomers (A), (B) and (C) is at least 30 wt. % and less than 70 wt. %.

3. The method of claim 1 wherein monomer (C) is selected from the group consisting of N,N- methylenebisacrylamide and N,N-methylenebismethacrylamide.

4. The method of claim 1 wherein the potassium alkali and the ammonium alkali are selected from the group consisting of potassium hydroxide, potassium carbonate, potassium bicarbonate, ammonia, ammonium hydroxide, ammonium carbonate and ammonium bicarbonate.

5. A plant growth medium comprising an aqueous gel including a crosslinked, water-absorbent, mixed salt polyacrylate, wherein the crosslinked, water-absorbent, mixed salt polyacrylate is prepared by mixing a monomer solution of (A) acrylate acid neutralized 70–100 mole percent with a potassium alkali and an ammonium alkali; (B) a styrene in an amount of 0& to 25% based on the weight of acrylate acid and (C) a water-miscible to water-soluble polyvinyl monomer in a combined concentration of (A), (B) and (C) of at least 30 wt. %; with water to form a mixed monomer solution wherein the monomers of the mixed monomer solution consist essentially of (A) and (B) and (C) and initiating polymerization of monomers (A), (B) and (C) such that during polymerization, the exothermic heat of reaction is substantially the only heat energy used to accomplish polymerization, cross-linking and to drive off sufficient water to obtain a solid cross-linked resin having a water content of 15 percent by weight or less.

6. The plant growth or plant preservation medium of claim 5, wherein the combined concentration of the monomers (A), (B) and (C) is at least 30 wt. % and less than 70 wt. %.

7. The plant growth or plant preservation medium of claim 5 wherein monomer (C) is selected from the group consisting of N,N-methylenebisacrylamide and N,N-methlenebismethacrylamide.

8. The plant growth or plant preservation medium of claim 5 wherein the potassium alkali and the ammonium alkali are selected from the group consisting of potassium hydroxide, potassium carbonate, potassium bicarbonate, ammonia, ammonium hydroxide, ammonium carbonate and ammonium bicarbonate.

9. A method of increasing the yield of transplanted crops comprising contacting a plant root with an aqueous gel comprising from about 0.4% to about 0.7% by weight of a mixed potassium and ammonium salt of a crosslinked, copolymerized or homopolymerized acrylate and covering the plant root and the aqueous salt of a crosslinked, copolymerized or homopolymerized acrylate is prepared by mixing a monomer solution of (A) acrylic acid neutralized 70–100 mole percent with a potassium alkali and an ammonium alkali; (B) styrene in an amount of 0% to 25% based on the weight of acrylic acid and (C) a water-miscible to water-soluble polyvinyl monomer in a combined concentration of (A), (B) and (C) of at least 30% wt. %; with water to form a mixed monomer solution and initiating polymerization of monomers (A), (B) and (C) such that during polymerization, the exothermix heat of reaction is substantially the only heat energy used to accomplish polymerization, cross-linking and to drive off sufficient water to obtain a solid cross-linked resin having a water content of 15 percent by weight or less.

10. The method of claim 9 wherein the combined concentration of the monomers (A), (B) and (C) is at least 30 wt. % and less than 70 wt. %.

11. The method of claim 9 wherein monomer (C) is selected from the group consisting of N,N-methylenebisacrylamide and N,N-methylenebismethacrylaide.

12. The method of claim 9 wherein the potassium alkali and the ammonium alkali are selected from the group consisting of potassium hydroxide, potassium carbonate, potassium bicarbonate, ammonia, ammonium hydroxide, ammonium carbonate and ammonium bicarbonate.

* * * * *